(12) United States Patent
Otsubo

(10) Patent No.: US 8,486,040 B2
(45) Date of Patent: Jul. 16, 2013

(54) WEARING ARTICLE

(75) Inventor: Toshifumi Otsubo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 423 days.

(21) Appl. No.: 12/921,612

(22) PCT Filed: Jan. 16, 2009

(86) PCT No.: PCT/JP2009/050581
§ 371 (c)(1),
(2), (4) Date: Nov. 21, 2010

(87) PCT Pub. No.: WO2009/116306
PCT Pub. Date: Sep. 24, 2009

(65) Prior Publication Data
US 2011/0060305 A1    Mar. 10, 2011

(30) Foreign Application Priority Data

Mar. 18, 2008  (JP) .................................. 2008-070281

(51) Int. Cl.
*A61F 13/15*  (2006.01)
(52) U.S. Cl.
USPC .............. 604/385.31; 604/385.21; 604/385.3; 604/396
(58) Field of Classification Search
USPC ........... 604/385.01, 385.101, 385.21, 385.22, 604/385.3, 385.31, 396
See application file for complete search history.

(56) References Cited

U.S. PATENT DOCUMENTS

| | | | | |
|---|---|---|---|---|
| 4,928,323 | A * | 5/1990 | Nathan | 2/406 |
| 6,231,558 | B1 * | 5/2001 | Mosley | 604/385.29 |
| 6,648,868 | B2 * | 11/2003 | Sayama et al. | 604/385.22 |
| 7,806,885 | B2 * | 10/2010 | Inoue et al. | 604/385.31 |
| 7,955,311 | B2 * | 6/2011 | Tanaka et al. | 604/385.3 |
| 2001/0049512 | A1 * | 12/2001 | Kawamura et al. | 604/312 |

FOREIGN PATENT DOCUMENTS

| | | |
|---|---|---|
| JP | 08117276 | 5/1996 |
| JP | 08132576 | 5/1996 |
| JP | 2000279444 | 10/2000 |
| JP | 2000513643 | 10/2000 |
| JP | 2006247009 | 9/2006 |
| WO | 9960971 | 12/1999 |

OTHER PUBLICATIONS

International Search Report for PCT/JP2009/050581 mailed Mar. 3, 2009.

* cited by examiner

*Primary Examiner* — Lynne Anderson
(74) *Attorney, Agent, or Firm* — Lowe Hauptman Ham & Berner, LLP

(57) ABSTRACT

A wearing article includes front and rear waist regions joined together. A joint strength of joint arrays along the front and rear waist regions is generally uniformed. A chassis is formed along front waist region's side edges and rear waist region's side edges with the joint arrays. A liquid-absorbent structure includes front and rear ends opposed to each other in a longitudinal direction and extending in a transverse direction. The front end is covered with a front waist sheet and the rear end is covered with a rear waist sheet. Along the respective joint arrays, the front and rear waist sheets are spaced from each other in the longitudinal direction.

6 Claims, 4 Drawing Sheets

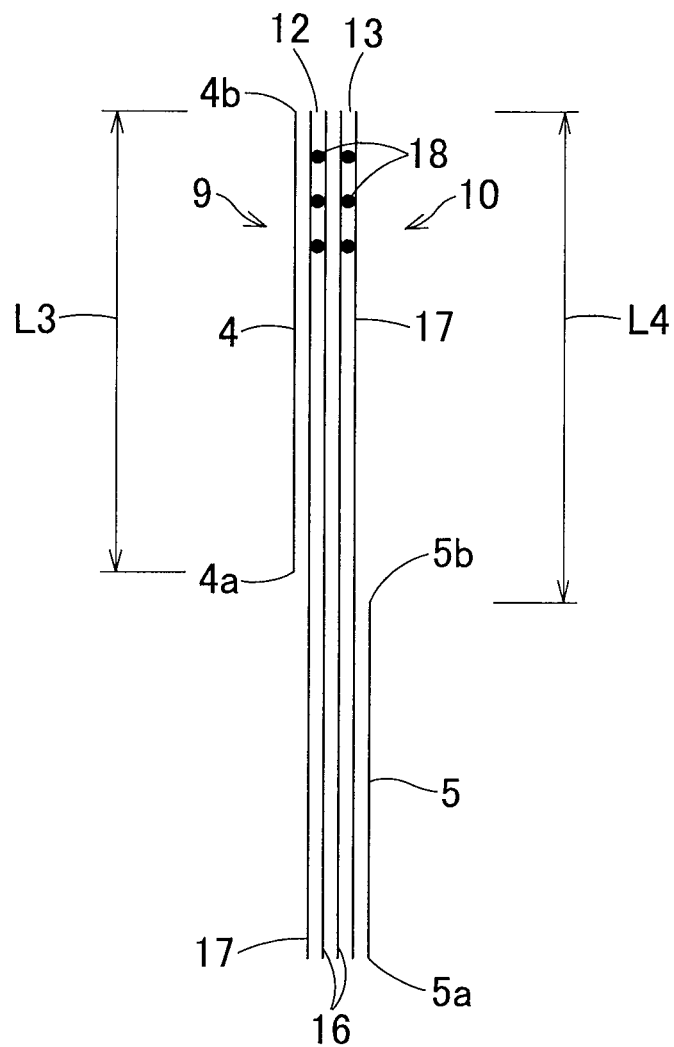

WEARING ARTICLE

RELATED APPLICATIONS

The present application is a national phase of PCT/JP2009/050581 filed Jan. 16, 2009, and claims priority from, Japanese Application Number 2008-070281, filed Mar. 18, 2008.

TECHNICAL FIELD

The present invention relates to wearing articles and more particularly to wearing articles such as disposable diapers, toilet-training pants or incontinent briefs.

RELATED ART

It is conventionally known to attach waist sheets to front and rear waist regions, respectively, for example, from the disclosure of JP 2006-247009 A (PATENT DOCUMENT 1). According to this PATENT DOCUMENT 1, the diaper has an inner sheet, an outer sheet and an absorbent structure attached to the skin-facing side of the inner sheet. Waist sheets are joined to the skin-facing side of the absorbent structure to cover front and rear ends of the absorbent structure, respectively. The absorbent structure is formed of wrapping pulp fibers as core material with tissue paper. By covering the front and rear ends of the absorbent structure with the waist sheets, respectively, falling out of the pulp fibers as the core material from the absorbent structure can be prevented.

Each of the inner and outer sheets is contoured by opposite side edges extending in a longitudinal direction and front and rear ends extending in a transverse direction. By joining the front waist region's side edges to the rear waist region's side edges, a waist-opening and a pair of leg-openings are formed and thereby a pull-on pant-type diaper is obtained. PATENT DOCUMENT 1: JP 2006-247009 A

DISCLOSURE OF THE INVENTION

Problem to be Solved by the Invention

In the case of the diaper disclosed by PATENT DOCUMENT 1, the front and rear waist sheets lie at a generally equal distance from the front and rear ends of the inner sheet. As a consequence, when the front waist region's side edges are joined to the rear waist region's side edges, the front and rear waist sheets are opposed and overlapped to each other along the respective joint arrays. In the vicinity of the front and rear ends of the chassis, the inner sheet overlaps itself because neither the front waist sheet nor the rear waist sheet is present in these regions. In other words, each of the joint arrays comprises a segment along which the inner sheet overlaps itself and a segment along which the front and rear waist sheets overlap each other. In the segment along which the inner sheet overlaps itself, the thickness of the joint array is defined by two sets of the inner and outer sheets, i.e., four sheets in total. In the segment along which the front and rear waist sheets overlap each other, the thickness of the joint array is defined by, in addition to the front and rear waist sheets, two sets of the inner and outer sheets, i.e., six sheets in total.

The joint array is formed by heat-sealing under an even pressure and, in consequence, if the number of sheets overlapping one on another is uneven, the joint strength is higher along the segment in which the number of sheets is relatively large and lower along the segment in which the number of sheets is relatively small. In other words, it is impossible to equalize the joint strength. Particularly in the vicinity of the leg-openings, the joint arrays are apt to be affected by the force tending to inactivate the joint arrays as the diaper wearer's lower body moves and, if the joint strength is insufficient, the front and rear waist regions may be eventually peeled off from each other along the joint arrays. On the other hand, the used diaper is usually rolled up to a size as small as possible for disposal after the front and rear waist regions have been peeled off along the joint arrays. If the joint strength is excessively high, it may be impossible to peel off the front and rear waist regions along the joint arrays of the used diaper and there is possibility that the diaper might be torn from unexpected region.

In view of the problem as has been described above, it is a principal object of the present invention to provide a wearing article improved so that a joint strength of joint arrays along which front and rear waist regions are joined together may be generally uniformed.

Measure to Solve the Problem

The object set forth above is achieved, according to the present invention, by an improvement in the wearing article comprising a chassis having a longitudinal direction, a transverse direction, a skin-facing inner side, a garment-facing outer side, a front waist region, a rear waist region and a crotch region extending in the longitudinal direction continuously between said front waist region and said rear waist region, and front and rear waist sheets attached to the front and rear waist regions, respectively, wherein the chassis is contoured by a pair of front waist region's side edges opposed to each other in the transverse direction and extending in the longitudinal direction, a pair of rear waist region's side edges opposed to each other in the transverse direction and extending in the longitudinal direction, a pair of crotch region's side edges extending between the pair of front waist region's side edges and the pair of rear waist region's side edges and front and rear end edges opposed to each other in the longitudinal direction and extending in the transverse direction and wherein the front waist region's side edges and the rear waist region's side edges are joined together along a pair of joint arrays to form a waist opening surrounded by the front and rear end edges and to form a pair of leg-openings surrounded by the crotch region's side edges.

The improvement according to the present invention is characterized in that the front waist sheet extends in the transverse direction from one of the front waist region's side edges to the other of the front waist region's side edges in the chassis, the rear waist sheet extends in the transverse direction from one of the rear waist region's side edges to the other of the rear waist region's side edges and the front and rear waist sheets are spaced from each other in the longitudinal direction in regions defined by the joint arrays.

The expression "spaced from each other" used herein includes not only the state in which a noticeable space is left between the front and rear waist sheets but also the state in which these two sheets share borders leaving substantially no space.

According to one preferred embodiment of the present invention, the front waist sheet or the rear waist sheet lies close to the waist-opening and the other lies close to the leg-openings.

According to another preferred embodiment of the present invention, the wearing article further includes a liquid-absorbent structure lying in the crotch region; and the liquid-absorbent structure includes front and rear ends opposed to each other in the longitudinal direction and extending in the transverse direction and covered with the front and rear waist sheets, respectively, and the front and rear waist sheets are joined to the chassis by the intermediary of the liquid-absorbent structure.

According to still another preferred embodiment of the present invention, a transverse center line bisecting a dimension of the liquid-absorbent structure in the longitudinal direction is placed nearer the front waist region than a transverse center line bisecting a dimension of the chassis in the longitudinal direction.

According to yet another preferred embodiment of the present invention, the front and rear waist sheets are attached to the skin-facing inner side of the chassis and the garment-facing outer side of the chassis.

According to further another preferred embodiment of the present invention, at least one of the front and rear waist sheets contains heat-sealable fibers and the joint arrays are formed by heat-sealing technique.

Effect of the Invention

In the regions defined by the respective joint arrays, the front and rear waist sheets are spaced from each other in the longitudinal direction to avoid the undesirable situation that the number of sheets might unacceptably increase and the joint strength might correspondingly increase. With the careful arrangement to avoid such problem, the present invention assures that the joint strength of the joint arrays can be generally equalized even when these joint arrays are formed under a given pressure.

The front waist sheet or rear waist sheet is placed to be close to the waist-opening and the other is placed to be close to the leg-openings. Both the waist-opening and the leg-openings define the ends of the joint arrays which are directly subject to the force tending to peel off the front and rear waist regions from each other and such force otherwise would easily peel off these two waist regions from each other. However, the above-described placement of the front and rear waist sheets serves to thicken the respective peripheral edges of the waist-opening and the leg-openings and to increase the joint strength in these regions. In this way, it is possible to prevent the joint arrays from being peeled off during use of the wearing article.

The wearing article further includes the liquid-absorbent structure of which the front and rear ends are covered with the front and rear waist sheets, respectively. The front and rear waist sheets serve to prevent the liquid-absorbent core material from falling out of the liquid-absorbent structure.

By placing the transverse center line of the liquid-absorbent structure nearer the front waist region than the transverse center line of the chassis, a liquid absorption power in the front waist region normally exposed to excretion of fluid can be improved. In addition, after the front waist region's side edges have been joined to the rear waist region's side edges, the front and rear ends of the liquid-absorbent structure are out of alignment. It is thereby assured that the front and rear waist sheets attached to cover the front and rear ends of the liquid-absorbent structure, respectively, do not overlap each other. In this way, it is possible to prevent the thickness of the joint arrays from becoming extremely uneven.

The front and rear waist sheets are attached to the skin-facing inner side or the garment-facing outer side so that the front and rear waist sheets may be attached to the chassis after the chassis has been formed. In this way, the process of making the wearing article can be simplified.

At least one of the front and rear waist sheets contains the heat-sealable fibers so that the joint arrays may be formed by heat-sealing technique. In this way, the joint arrays can be easily formed at a low cost.

BRIEF DESCRIPTION OF THE DRAWINGS

FIG. 5 is a sectional view taken along the line V-V in FIG. 1.

Figure 1:
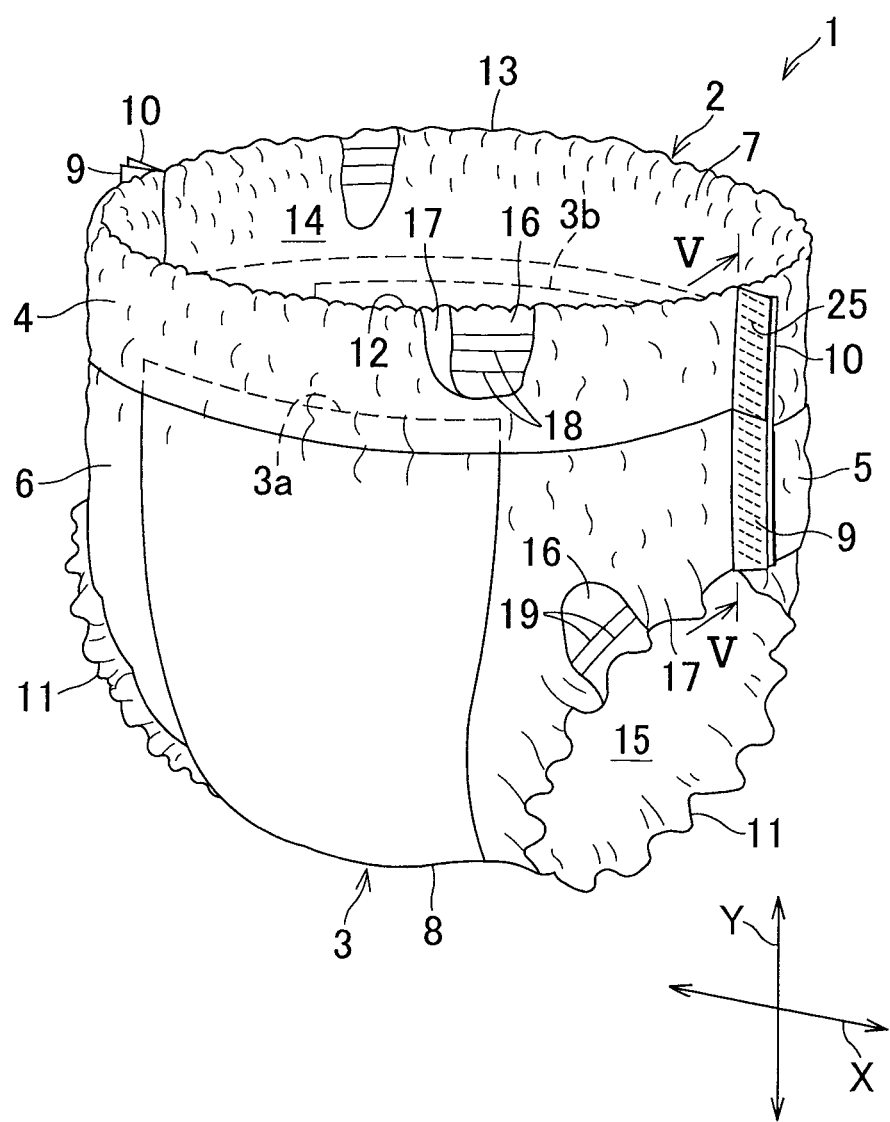
FIG. 1 is a perspective view of a diaper.

IDENTIFICATION OF REFERENCE NUMERALS
USED IN THE DRAWINGS 1 diaper
2 chassis
3 liquid-absorbent structure
4 front waist sheet
5 rear waist sheet
6 front waist region
7 rear waist region
8 crotch region
9 front waist region's side edges
10 rear waist region's side edges
11 crotch region's side edges
12 front end edge
13 rear end edge
14 waist-opening
15 leg-openings
25 joints

DETAILED DESCRIPTION OF THE PREFERRED
EMBODIMENTS

Details of the present invention will be more fully understood from the description of a disposable diaper as a typical embodiment of the wearing article according to the present invention given hereunder in reference to the accompanying drawings.

FIG. 1 is a perspective view showing the diaper 1 put on the wearer's body and is partially cutaway for convenience of illustration. As will be understood from FIG. 1, the diaper 1 comprises a liquid-absorbent chassis 2, a liquid-absorbent structure 3 and front and rear waist sheets 4, 5. The chassis 2 is shaped in pull-on pants type and includes a front waist region 6, a rear waist region 7 and a crotch region 8 extending between the front and rear waist regions 6, 7. A direction extending from the front waist region 6 across the crotch region to the rear waist region 7 is designated herein as a longitudinal direction Y and a direction extending orthogonally to the longitudinal direction Y is designated herein as a transverse direction X.

The chassis 2 includes a pair of front waist region's side edges 9 opposed to each other in the transverse direction X and extending in the longitudinal direction Y in the front waist region 6, a pair of rear waist region's side edges 10 opposed to each other in the transverse direction X and extending in the longitudinal direction Y in the rear waist region 7, a pair of crotch region's side edges 11 opposed to each other in the transverse direction X and extending in the longitudinal direction Y in the crotch region 6, and front and rear end edges 12, 13 opposed to each other in the longitudinal direction Y and extending in the transverse direction X. The front waist region's side edges 9 and the rear waist region's side edges 10 are sealed together to form a plurality of joints 25 so that a waist-opening 14 may be formed in a region surrounded by the front and rear end edges 12, 13 and a pair of leg-openings 15 may be formed in regions surrounded by the crotch region's side edges 11, respectively.

The chassis 2 is formed of an inner sheet 16 defining a skin-facing inner side of the diaper 1 and an outer sheet 17 defining a garment-facing outer side of the diaper 1. Two or more waist-surrounding elastic members 18 are sandwiched between the inner and outer sheets 16, 17 to extend along a peripheral edge of the waist-opening 14 and two or more leg-surrounding elastic members 19 extend along peripheral edges of the respective leg-openings 15. These elastic members 18, 19 are bonded under tension to at least one of the inner and outer sheets 16, 17 by adhesive (not shown). The liquid-absorbent structure 3 is provided on the garment-facing outer side of the outer sheet 17 so that the liquid-absorbent structure 3 may extend across at least in the crotch region 8 or may extend across the crotch region 8 into the front and rear waist regions 6, 7.

The inner and outer sheets 16, 17 may be formed of a liquid-pervious nonwoven fabric and at least one of the inner and outer sheets 16, 17 may contain heat sealable fibers such as polyolefin fibers. Such heat sealable fibers contained in the nonwoven fabric allows the joints 25 to be formed by pressurizing the front waist region's side edges 9, 9 and the rear waist region's side edges 10, 10 opposite to each other under heating.

Figure 2:
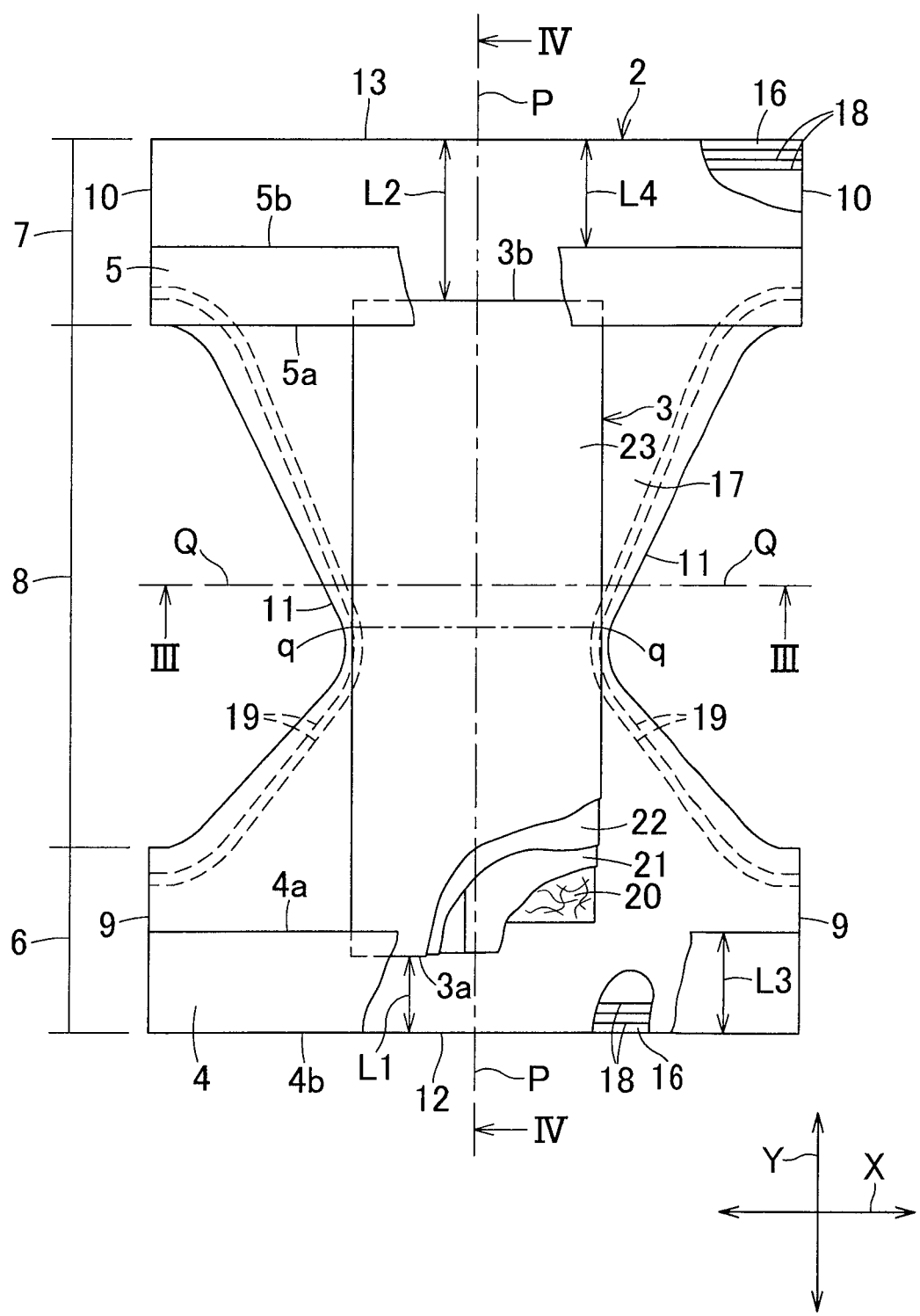
FIG. 2 is a flatly developed view of the diaper.
Figure 3:
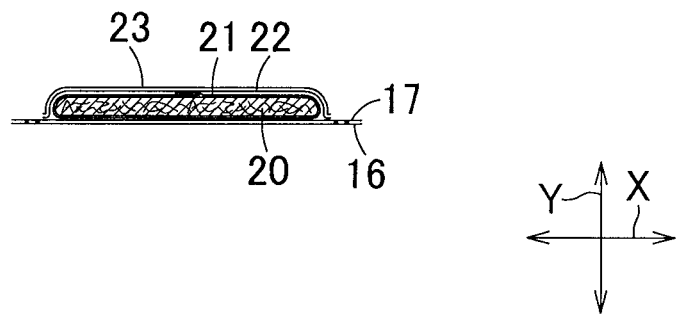
FIG. 3 is a sectional view taken along the line III-III in FIG. 2.
Figure 4:
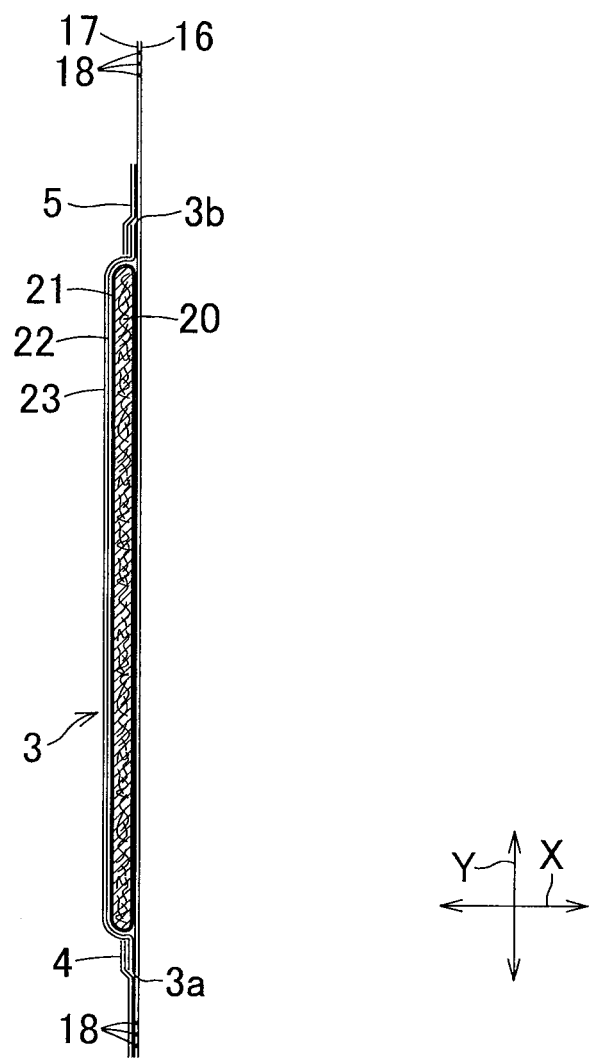
FIG. 4 is a sectional view taken along the line IV-IV in FIG. 2.

FIG. 2 is a plan view of the diaper 1 having been developed in the longitudinal direction Y as well as in the transverse direction X after the front waist region's side edges 9 and the rear waist region's side edges 10 peeled off one from another at the joints 25, FIG. 3 is a sectional view taken along the line in FIG. 2 and FIG. 4 is a sectional view taken along the line IV-IV in FIG. 2. In FIGS. 2 through 4, the front waist region 6, the rear waist region 7 and the crotch region 8 are kept to lie in the same plane by nullifying contractile force of the respective elastic members wherein FIG. 2 is partially cutaway for convenience of illustration. The diaper 1 has a longitudinal center line P-P bisecting a dimension of the diaper 1 in the transverse direction X and a transverse center line Q-Q bisecting a dimension of the diaper 1 in the longitudinal direction Y wherein the diaper 1 is symmetric about the longitudinal center line P-P. The crotch region's side edges 11 are formed to curve with respect to the front and rear waist regions' side edges 9, 10 convexly toward the longitudinal center line P-P and, in consequence, the chassis 2 has a concave shape curved inwardly.

The liquid-absorbent structure 3 is provided on the garment-facing outer side of the chassis 2 to face the outer sheet 17. The liquid-absorbent structure 3 comprises a liquid-absorbent core material 20, a liquid absorbent and dispersant sheet 21 such as a tissue paper, a leak-barrier sheet provided on the garment-facing outer side of the liquid-absorbent/dispersant sheet 21 and a cover sheet 23 adapted to cover the leak-barrier sheet 22. The leak-barrier sheet 22 may be formed, for example, by a moisture-pervious plastic film and serves to prevent bodily fluids once absorbed by the core material 20 from leaking out from the diaper 1. The core may be formed, for example, of mixture of fluff pulp fibers and super-absorbent polymer particles and the cover sheet 23 may be formed, for example, of an air-permeable nonwoven fabric.

The liquid-absorbent structure 3 includes front and rear ends 3a, 3b opposed to each other in the longitudinal direction Y and extend in the transverse direction X. The front end 3a lies in the front waist region 6 and the rear end 3b lies in the rear waist region 7. The front end 3a is covered with a front waist sheet 4 and the rear end 3b is covered with a rear waist sheet 5. The front waist sheet 3a extends from one of the front waist region's side edges 9 to the other of the front waist region's side edges 9 in the transverse direction X and the rear waist sheet 5 extends from one of the rear waist region' side edges 10 to the other of the rear waist region's side edges 10 in the transverse direction X. These front and rear waist sheets 4, 5 are respectively joined to the outer sheet 17 by adhesive bonding or sealing technique through the intermediary of the liquid-absorbent structure 3. The front and rear ends 3a, 3b of the liquid-absorbent structure 3 may be covered with the front and rear waist sheets 4, 5, respectively, to prevent the core material 20 from falling out of the liquid-absorbent structure 3 and, at the same time, to reinforce the front and rear waist regions. In the transverse direction X, the core material 20 is wrapped with the liquid-absorbent/dispersant sheet 21, on one hand, and the leak-barrier sheet 22 as well as the cover sheet 23 overlapping the liquid-absorbent/dispersant sheet 21 is joined to the outer sheet 17 by adhesive bonding or sealing technique, on the other hand. With such unique arrangement, the core material 20 would not fall off in the transverse direction X.

The liquid-absorbent structure 3 has the transverse center line q-q bisecting its dimension in the longitudinal direction Y and this center line q-q is set to be placed nearer the front waist region 6 than the transverse center line Q-Q. Consequently, a dimension L2 from the rear end edge 13 of the chassis 2 to the rear end 3b of the liquid-absorbent structure 3 is longer than a dimension L1 from the front end edge 12 of the chassis 2 to the front end 3a of the liquid-absorbent structure 3. A dimension L3 from an inner end 4a to an outer end 4b of the front waist sheet 4 is set to be equal to or smaller than a dimension L4 from the rear end edge 13 to an outer end 5b of the rear waist sheet 5.

FIG. 5 is a sectional view taken along the line V-V in FIG. 1, showing the joints 25 at which the front waist region's side edges 9 are joined to the rear waist region's side edges 10. After the front and rear waist regions have been joined together along the respective side edges 9, 10 thereof so that respective halves of the folded inner sheet 16 are put flat together and the front and rear end edges 12, 13 are opposed to each other, the front waist sheet 4 lies along the front end edge 12 and the rear waist sheet 5 lies nearer the crotch region's side edges 11 than the front waist sheet 4, i.e., downward from the front waist sheet 4 as viewed in the longitudinal direction Y. The front and rear waist sheets 4, 5 never overlap each other since the dimension L3 of the front waist sheet 4 in the longitudinal direction Y is set to be equal to or smaller than the dimension L4 from the rear end edge 13 to the outer end 5b of the rear waist sheet 5. Consequentially, two sheets of each of the inner and outer sheets 16, 17 and the front waist sheet 4, i.e., five sheets in total overlap one upon another in the upper region (as viewed in FIG. 1) of the joint array 25, on one hand, and two sheets of each of the inner and outer sheets 16, 17 and the rear waist sheet 5, i.e., five sheets in total overlap one upon another in the lower region of the joint array 25, on the other hand. In the middle region of the joint array 25 in which neither the front waist sheet 4 nor the rear waist sheet 5 is present, two sheets of each of the inner and outer sheets 16, 17, i.e., four sheets in total overlap each other.

The number of the sheets overlapping in the region defined by the joint array 25 is five at the most and four at the minimum and a difference between the maximum and the minimum is one. As a consequence, the number of the sheets overlapping one upon another in the region defined by the joint array 25 would not locally different at an unacceptable degree. In this way, a generally uniform thickness can be assured in the region of the joint array 25. In other words, the region defined by the joint array 25 is substantially free from any noticeable unevenness. By making the thickness of the region defined by the joint array 25 generally even, it is possible to prevent the joint strength in this region from locally and noticeably increasing or decreasing.

The front waist sheet 4 is attached to the chassis 2 so that the outer end 4b thereof may coincide with the front end edge 12 of the chassis 2. As a result, the diaper 1 becomes appropriately thicker and has correspondingly higher joint strength in the vicinity of the front end edge 12 than in the region in which the front waist sheet 4 is not present. Considering that the waist-opening 14 is partially defined by this front end edge 12, the front end edge 12 and the vicinity thereof are apt to be directly subject to the force tending to peel off the front and rear waist regions' side edges 9, 10 one from another as the diaper 1 is put on the diaper wearer's body and/or the diaper wearer's body moves. However, the joint strength in the vicinity of the front end edge 12 can be appropriately increased as has been described above and therefore the respective pairs of the front and rear waist regions' side edges 9, 10 would not begin to be peeled off one from another at the front end edge 12.

The rear waist sheet 5 is attached to the chassis 2 so that the inner end 5a thereof may coincide with a boundary line between the rear waist region 6 and the crotch region 8. With such location, the joint strength can be increased in the region of the joint array 25 adapted to participate in formation of the leg-opening 15 compared to the region in which the rear waist sheet 5 is not present. In the vicinity of the leg-opening 15, the joint array 25 is apt to be subject to the force tending to peel off them as the diaper wearer's legs move. However, the joint strength in the vicinity of the leg-opening may be increased to prevent such peeling of the joints 25.

In the vertically middle region of the joint array 25, the front and rear waist sheets 4, 5 do not overlap with each other but share borders with each other or are spaced from each other. Consequentially, no increase of the joint strength occurs in this middle region in comparison with the joint strength in the upper and lower regions of the joint array 25. This is advantageous in that, when it is desired to peel off the front and rear waist regions from each other along the joint arrays 25 after used and then to roll up the diaper 1 for disposal, a pulling force may be concentrate on the region in which the front and rear waist sheets 4, 5 overlap each other to peel the front and rear waist regions apart from each other smoothly. In this way, the front and rear waist regions can be smoothly peeled apart from each other without tearing the diaper 1 from any unintentional region along the joint arrays 25.

By attaching the front and rear waist sheets 4, 5 to the chassis 2 to be spaced from each other or merely share borders with each other in longitudinal direction Y as has been described above, the thickness of the joint array 25 and, therefore, the joint strength of the joint array 25 can be maintained substantially at an even level without varying intervals or patterns of the individual joints 25 in the longitudinal direction Y. As it will be apparent from FIG. 1, the individual joints 25 may be arranged at the regular intervals and in the same pattern in the longitudinal direction Y. In this way, compared to the case in which the joints 25 must be arranged in an irregular pattern, cost as well as time needed to make the diaper may be reduced.

The number of sheets overlapping one on another in the region defined by the joint array 25 can be effectively restricted and therefore any feeling of incompatibility which would be experienced by the diaper wearer can be alleviated. Specifically, if the number of sheets overlapping one on another in the region defined by the joint array 25 exceeds the allowable range, stiffness of this region as a whole will cause the diaper wearer to experience noticeable feeling of incompatibility. The stiffness will be further increased by heat-sealing or bonding these sheets until the diaper wearer will suffer from skin trouble. According to the present invention, the number of sheets overlapping one on another may be minimized to protect the diaper wearer from such skin trouble.

According to the present invention, the joint strength of the joint array 25 is set to a range of 15 to 25N/25 mm in the regions in which the front and rear waist sheets 4, 5 lie, respectively. The joint strength is measured by preparing a joint array 25 having a length dimension of about 25 mm in the longitudinal direction Y and a length dimension of about 30 mm in the transverse direction X as a sample for measurement. The sample is formed to extend from the front waist region 6 to the rear waist region 7 by the intermediary of the joint array 25. The measurement is carried out by clamping the ends of the sample on the sides of the front and rear waist regions 6, 7, respectively, and pulling the sample in a direction in which the front and rear waist regions 6, 7 are spaced apart from each other. More specifically, an inter-chuck distance is set to about 10 mm and a peeling rate is set to 300 mm/min.

While the front waist sheet 4 is placed near the waist-opening 14 and the rear waist sheet 5 is placed near the side of the leg-openings 15 in the embodiment as has been described above, it is possible to place the front waist sheet 4 near the leg-openings 15 and to place the rear waist sheet 5 near the waist-opening 14. It is also possible to attach only one of the front and rear waist sheets to the chassis 2.

The front and rear waist regions 6, 7 are joined together along the respective joint arrays 25 by heat-sealing according to the embodiment as has been described above, it is possible to join these waist regions 6, 7 together by ultrasonic sealing technique or adhesive. In this case, it will be unnecessary to use heat-sealable material for the front and rear waist sheets 4, 5. It should be appreciated that the joint array 25 is formed preferably by heat-sealing from the viewpoint of simplification and cost reduction of the method.

While the liquid-absorbent structure 3 is attached to the outer sheet 17 according to the embodiment as has been described above, it is possible to attach the liquid-absorbent structure to the inner sheet 16. In this case, the front and rear waist sheets 4, 5 may be bonded to the inner sheet 16 by the intermediary of the liquid-absorbent structure 3. The liquid-absorbent structure 3 previously obtained in the step which is dependent from the chassis 2 may be attached to the skin-facing inner side of the chassis 2 or to the garment-facing outer side to reduce the manufacturing cost.

The invention claimed is:

1. A wearing article comprising a chassis having a longitudinal direction, a transverse direction, a skin-facing inner side, a garment-facing outer side, a front waist region, a rear waist region and a crotch region extending in said longitudinal direction continuously between said front waist region and said rear waist region, and front and rear waist sheets attached to said front and rear waist regions, respectively, wherein said chassis is contoured by a pair of front waist region's side edges opposed to each other in said transverse direction and extending in said longitudinal direction, a pair of rear waist region's side edges opposed to each other in said transverse direction and extending in said longitudinal direction, a pair of crotch region's side edges extending between said pair of front waist region's side edges and said pair of rear waist region's side edges and front and rear end edges opposed to each other in said longitudinal direction and extending in said transverse direction and wherein said front waist region's side edges and said rear waist region's side edges are joined together along a pair of joint arrays to form a waist opening surrounded by said front and rear end edges and to form a pair of leg-openings surrounded by said crotch region's side edges, said wearing article wherein:

said front waist sheet extends in said transverse direction from one of said front waist region's side edges to other of said front waist region's side edges in said chassis, said rear waist sheet extends in said transverse direction from one of said rear waist region's side edges to other of said rear waist region's side edges and said front and rear waist sheets are spaced from each other in said longitudinal direction in regions defined by said joint arrays.

2. The wearing article defined by claim 1 wherein said front waist sheet or said rear waist sheet lies close to said waist-opening and other lies close to said leg-openings.

3. The wearing article defined by claim 1 wherein:
said wearing article further includes a liquid-absorbent structure lying in said crotch region; and
said liquid-absorbent structure includes front and rear ends opposed to each other in said longitudinal direction and extending in said transverse direction and covered with said front and rear waist sheets, respectively, and said front and rear waist sheets are joined to said chassis by an intermediary of said liquid-absorbent structure.

4. The wearing article defined by claim 1 wherein a transverse center line bisecting a dimension of said liquid-absorbent structure in said longitudinal direction is placed nearer said front waist region than a transverse center line bisecting a dimension of said chassis in said longitudinal direction.

5. The wearing article defined by claim 1 wherein said front and rear waist sheets are attached to said skin-facing inner side of said chassis or said garment-facing outer side.

6. The wearing article defined by claim 1 wherein at least one of said front and rear waist sheets contains heat-sealable fibers and said joint arrays are formed by heat-sealing technique.

* * * * *